United States Patent
Saul et al.

(10) Patent No.: US 7,229,783 B2
(45) Date of Patent: Jun. 12, 2007

(54) METHOD FOR MONITORING HYGIENE

(75) Inventors: Steven J. Saul, Arlington, MA (US); Cheryl B. Francisco, Fairhaven, MA (US); Robert J. Markovsky, Brentwood, NH (US); Robert S. Salter, Reading, MA (US); Stanley E. Charm, Boston, MA (US)

(73) Assignee: Charm Sciences, Inc., Lawrence, MA (US)

( * ) Notice: Subject to any disclaimer, the term of this patent is extended or adjusted under 35 U.S.C. 154(b) by 248 days.

(21) Appl. No.: 10/343,582

(22) PCT Filed: Aug. 1, 2001

(86) PCT No.: PCT/US01/24054

§ 371 (c)(1), (2), (4) Date: Aug. 1, 2003

(87) PCT Pub. No.: WO02/10708

PCT Pub. Date: Feb. 7, 2002

(65) Prior Publication Data

US 2004/0028608 A1 Feb. 12, 2004

Related U.S. Application Data

(60) Provisional application No. 60/267,173, filed on Feb. 8, 2001, provisional application No. 60/228,369, filed on Aug. 28, 2000, provisional application No. 60/222,365, filed on Aug. 1, 2000.

(51) Int. Cl.
*C12Q 1/22* (2006.01)

(52) U.S. Cl. ............................. 435/31; 435/14

(58) Field of Classification Search ............ None
See application file for complete search history.

(56) References Cited

U.S. PATENT DOCUMENTS

| | | | |
|---|---|---|---|
| 4,098,574 A | 7/1978 | Dappen | |
| 4,211,845 A * | 7/1980 | Genshaw et al. | 435/14 |
| 4,353,891 A * | 10/1982 | Guggenheim et al. | 424/50 |
| 5,436,133 A | 7/1995 | Fujita et al. | |
| 5,563,042 A | 10/1996 | Phillips et al. | |
| 5,827,675 A | 10/1998 | Skiffington et al. | |
| 5,827,715 A | 10/1998 | Ishii et al. | |
| 5,965,453 A | 10/1999 | Skiffington et al. | |
| 5,985,675 A | 11/1999 | Charm et al. | |
| 6,001,658 A | 12/1999 | Fredrickson | |
| D419,439 S | 1/2000 | Markovsky et al. | |
| 6,043,047 A | 3/2000 | Foote et al. | |
| 6,180,395 B1 | 1/2001 | Skiffington et al. | |
| 6,265,179 B1 | 7/2001 | Zhou et al. | |
| 6,319,466 B1 | 11/2001 | Markovsky et al. | |
| 6,475,805 B1 | 11/2002 | Charm et al. | |

2002/0037590 A1 3/2002 Grant et al.

FOREIGN PATENT DOCUMENTS

| | | |
|---|---|---|
| EP | 0 790 302 A1 | 8/1997 |
| EP | 0 695 363 B1 | 9/1997 |
| WO | WO 94/25619 | 11/1994 |
| WO | WO 95/25948 | 9/1995 |
| WO | WO 97/03209 | 1/1997 |
| WO | WO 97/23596 | 7/1997 |
| WO | WO 98/27196 | 6/1998 |
| WO | WO 99/31218 | 6/1999 |
| WO | WO 00/36139 | 6/2000 |

OTHER PUBLICATIONS

Cury JA, Rebello MAB, Del Bel Cury AA (Oct. 1997) Caries Research 31, 356-360.*
Dubois et al. (Mar. 1956) Anal chem. 28 (3), 350-356.*
Somogyi (1945) JBC 160, 61-68.*
U.S. Appl. No. 09/961,998, filed Sep. 24, 2001, Markovsky et al.
U.S. Appl. No. 10/014,154, filed Dec. 6, 2001, Skiffington et al.
Conrath, N., et al, "A novel enzyme sensor for the determination of inorganic phosphate," *Analytica Chimica Acta*, Jan. 25, 1995, vol. 309, pp. 47-52, Münster, Germany.
Hüwel, S., et al., "Production and Stabilization of Pure Maltose Phosphorylase from *Lactobacillus brevis* for Sensing Inorganic Phosphaste$^\alpha$," *Institute of Chemical and Biochemical Sensor Research and Department of Biochemistry*, University of Münster, 1996, pp. 701-706, Münster, Germany.
Hüwel, Stephan et al., "Maltose phosphorylase from *Lactobacillus brevis*: Purification , Characterization, and application in a biosensor for *ortho*-phospate," *Enzyme and Microbial Technology*, 1997, vol. 21, pp. 413-420, New York, NY USA.
"P$_i$Per™ Phosphate Assay Kit (P-22061)," *Molecular Probes. Product Information*, Mar. 24, 2000, pp. 1-6, Eugene, Oregon.
Handbook of Fluorescent Probes and Research Chemicals, "Principle of the P (*i*) Per Phosphaste Assay Kit," Apr. 14, 2000, p. 1, http://www.probes.com/handbook/figures/1021.html.
Sugiura, Y., et al., "Purification, Enzymatic Properties, and Active Site Environment of a Novel Managanese (III)-containing Acid Phosphatase," *The Journal of Biological Chemistry*, vol. 256, No. 20, pp. 10664-10670, Oct. 25, 1981, USA.

(Continued)

*Primary Examiner*—Ralph Gitomer
(74) *Attorney, Agent, or Firm*—Leslie Meyer-Leon; Richard J. Long

(57) ABSTRACT

A test method and test device for hygiene monitoring of a test sample from a biological material or a surface with a biological material to detect the presence of phosphate and glucose as a measure of hygiene by employing a swab-type, puncturable-membrane test apparatus or a lateral-flow or capillary-flow test apparatus.

62 Claims, 6 Drawing Sheets

OTHER PUBLICATIONS

Masayuku, N., "Hygiene Monitoring Kit Konica Swab'N 'Check," *Konica Technical Report*, vol. 9 Jan. 1996, pp. 113-116, pp. 1-3.

Analytical Biochemistry, "*An Enzymatic Method for the Determination of Maltose in the Presence of Other Oligosaccharides*," vol. 57, pp. 303-305 (1974).

Bailey, J.M. et al., Studies on Mutarotases, "*Purification and Properties of a Mutarotase from Higher Plants*," The Journal of Biological Chemistry, vol. 242, No. 19, pp. 4263-4269, Sep. 25, 1967, USA.

Calzyme Laboratories, Inc., "*Mutarotase (Aldose I-Empimerase) Porcine Kidney*," (Aldose I-epimerase; EC 5.1.3.3).

Tsumuray, Y, et al., Substrate-Induced Activation of Maltose Phosphorylase: Interaction with the Anomeric Hydroxyl Group of α-Maltose and α-D-Glucose Controls the Enzyme's Glucosyltransferase Activity[I], *Archives of Biochemistry and Biophysics*, vol. 281, No. 1, pp. 58-65, Aug. 15, (1990).

Johnson J. et al "Use of Purified Amyloglucosidase for the Specific Determination of Total Carbohydrate Content of Rat Liver Homogenate in a Single Step" *Analytical Biochemistry*, 1979, vol. 98, pp. 47-52, Omaha, Nebraska 68105, USA.

* cited by examiner

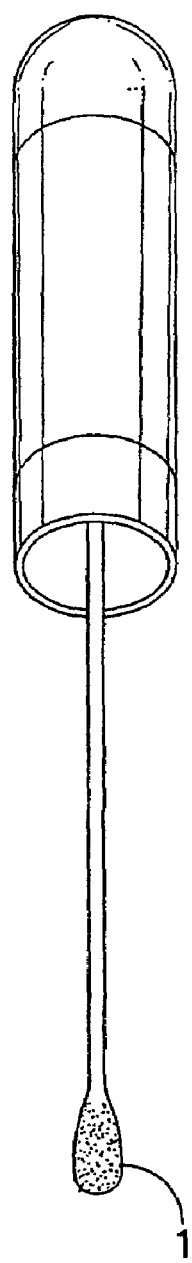
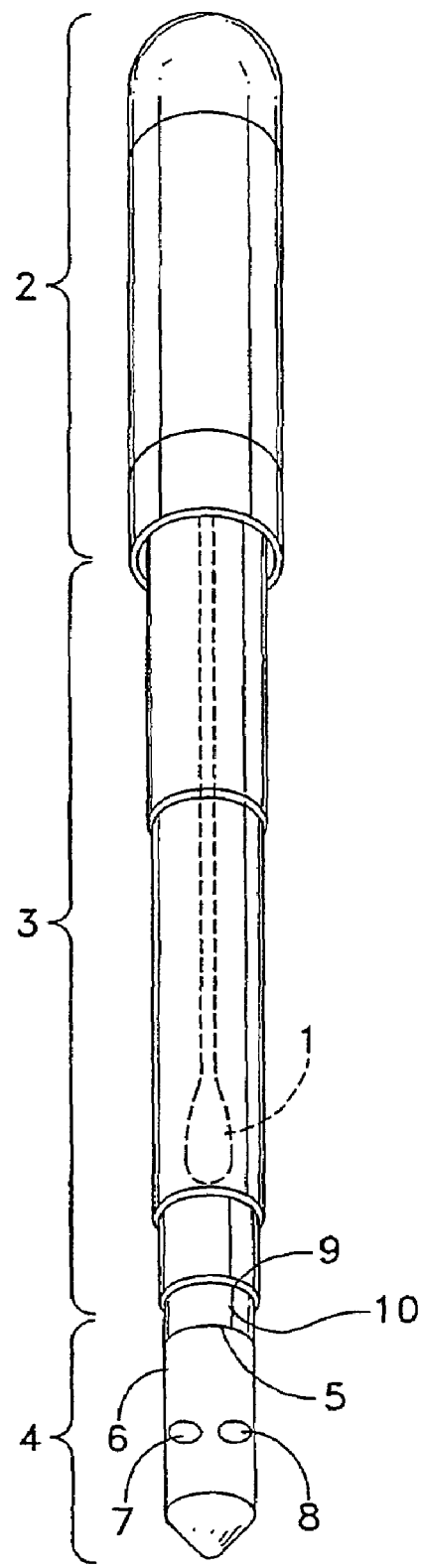
FIG. 3A
FIG. 3B

METHOD FOR MONITORING HYGIENE

REFERENCE TO PRIOR APPLICATIONS

The present application claims the benefit of International Application PCT/US01/24054, filed Aug. 1, 2001, which claims the benefit of U.S. Provisional Patent Application Ser. No. 60/222,365, filed Aug. 1, 2000; and U.S. Provisional Patent Application Ser. No. 60/228,369, filed Aug. 28, 2000; and U.S. Provisional Patent Application Ser. No. 60/267,173, filed Feb. 8, 2001; the contents of each of these provisional applications is hereby incorporated by reference in their entirety.

BACKGROUND OF THE INVENTION

Cleanliness in industrial and health care settings is critical. The surfaces of equipment used for food handling, storage, or processing are major sources of microbial contamination. Such contamination can lead to decreased shelf life of products and, if pathogens are present, transmission of disease. Microbial colonies develop rapidly. Continuous monitoring of surfaces, e.g., hygiene monitoring, can help protect against the spread of disease.

Historically, microbial culturing was used to determine the presence of microorganisms. However, culturing is time consuming and, therefore, the necessary "real time" feedback to sanitation and food preparation personnel is not available. As a result, food exposed to surfaces which were later found to contain potentially harmful microorganisms could enter the food supply.

Lateral-flow chromatographic test strips have been used for a variety of diagnostic purposes. The test described herein utilizes a lateral-flow test strip to provide a means for rapid, sensitive, user-friendly, hygiene monitoring of surfaces. Material swabbed from a surface can be detected by reactions involving the pathways described herein.

Recent attention has focused on the problems of biofilms. Biofilms are created when microorganisms land on a surface and attach to its microscopic cracks and crevices. Almost immediately, the organism begins to produce a polysaccharide-like material which in hours acts as a glue to stick bacteria and viruses to the surface. Biofilms are more resistant to routine sanitizing techniques than are their free-living counterparts. It is, therefore, critical to generate rapid results, preferably within a few minutes.

Food residues on surfaces are nutrients for rapid growth of microorganisms and the potentially resultant biofilm. Such food residues are also a source of cross-contamination to other food products later exposed to the same contact surface. Therefore, proper hygiene monitoring of a surface should include detection of a broad range of contaminants, including both biofilms and residual food.

During the 1990s various rapid and efficient test methods and apparatuses were developed for the detection of contamination on surfaces. Such methods do not detect microbes directly but instead detect markers, such as ATP, which are indicative of either the presence of microbes or the existence of residual food contamination of a surface.

One such apparatus is the POCKETSWAB® (POCKETSWAB® is a registered trademark of Charm Sciences, Inc. of Lawrence, Mass.), which rapidly and efficiently detects ATP on surfaces. The POCKETSWAB® apparatus detects ATP through the reaction of luciferin and luciferase, which, in the presence of ATP, emits light. Light emission is measured using a luminometer. It is desired, and the primary object of this invention, to provide a rapid, visual test for hygiene monitoring, and thereby avoid the need for a luminometer or other reader.

There are various tests available in the field which provide a rapid and visual result, thereby reflecting the degree of surface cleanliness. Such tests are of interest for use in, for example, restaurants and supermarkets, where an instrument for reading results would not be acceptable, either because of the large volume needed or because they could not be secured, or lack ease of use.

One such test is marketed by Celsis International, PLC of Cambridge, United Kingdom, under the trademark Spotcheckä. The SPOTCHECK™ employs a cyclic "comproproportionation" reaction to detect ATP (see U.S. Pat. No. 6,043,047, issued Mar. 28, 2000, and PCT International Publication No. WO 00/36139, published Jun. 22, 2000).

One example of a method for detection of inorganic phosphate is described by N. Conrath et al, "A novel enzyme sensor for the determination of inorganic phosphate", Analytica Chimica Acta 309 (195) 47–52 (1995), which is incorporated herein by this reference. That method, however, requires skilled laboratory personnel, is time consuming and requires equipment.

It is an object of this invention is to provide a broad-spectrum test to rapidly monitor the hygiene of a surface by detecting a variety of organic and inorganic materials, food residues and microorganisms.

SUMMARY OF THE INVENTION

A new and improved user friendly, broad spectrum, test apparatus, system and method adapted to provide a visual determination of surface contamination is the object of the current invention. The purpose of the test is to rapidly—within one minute—detect the presence of certain biological materials that are indicators of improper or inadequate sanitation and cleanliness. Test results are qualitative; a positive result indicates presence of residue and need to clean.

The invention comprises a method for the rapid, colorimetric determination of hygiene monitoring of surface contamination, which method comprises adding to a sample containing phosphate a phosphorylase enzyme and a carbohydrate substrate to provide a reaction product of free glucose and phosphate bound to a saccharide; and detecting said free glucose in a colorimetric reaction as a measure of surface contamination. Phosphorylases are enzymes that help catalyze cleavage of a bond by orthophosphate. In the case of maltose, maltose phosphorylase cleaves the carbon-oxygen linkage between glucose molecules to produce glucose and glucose-1-phosphate. That is, a phosphorylase enzyme such as maltose phosphorylase, and carbohydrate substrate, such as maltose, react with phosphate from the sample to produce α-D-glucose and β-D-glucose-1-phosphate.

The invention also comprises a method for the rapid, colorimetric determination of hygiene monitoring comprising adding to a sample containing phosphate maltose and maltose phosphorylase and detecting the amount of glucose or phosphate in a colorimetric reaction as a measure of surface contamination.

BRIEF DESCRIPTION OF THE DRAWINGS

FIG. 3A is a schematic view of the VERICLEEN™ swab removed from the test device;

FIG. 3B is a side perspective, see-through view of the VERICLEEN™ swab;

DESCRIPTION OF THE EMBODIMENTS

Figure 1:
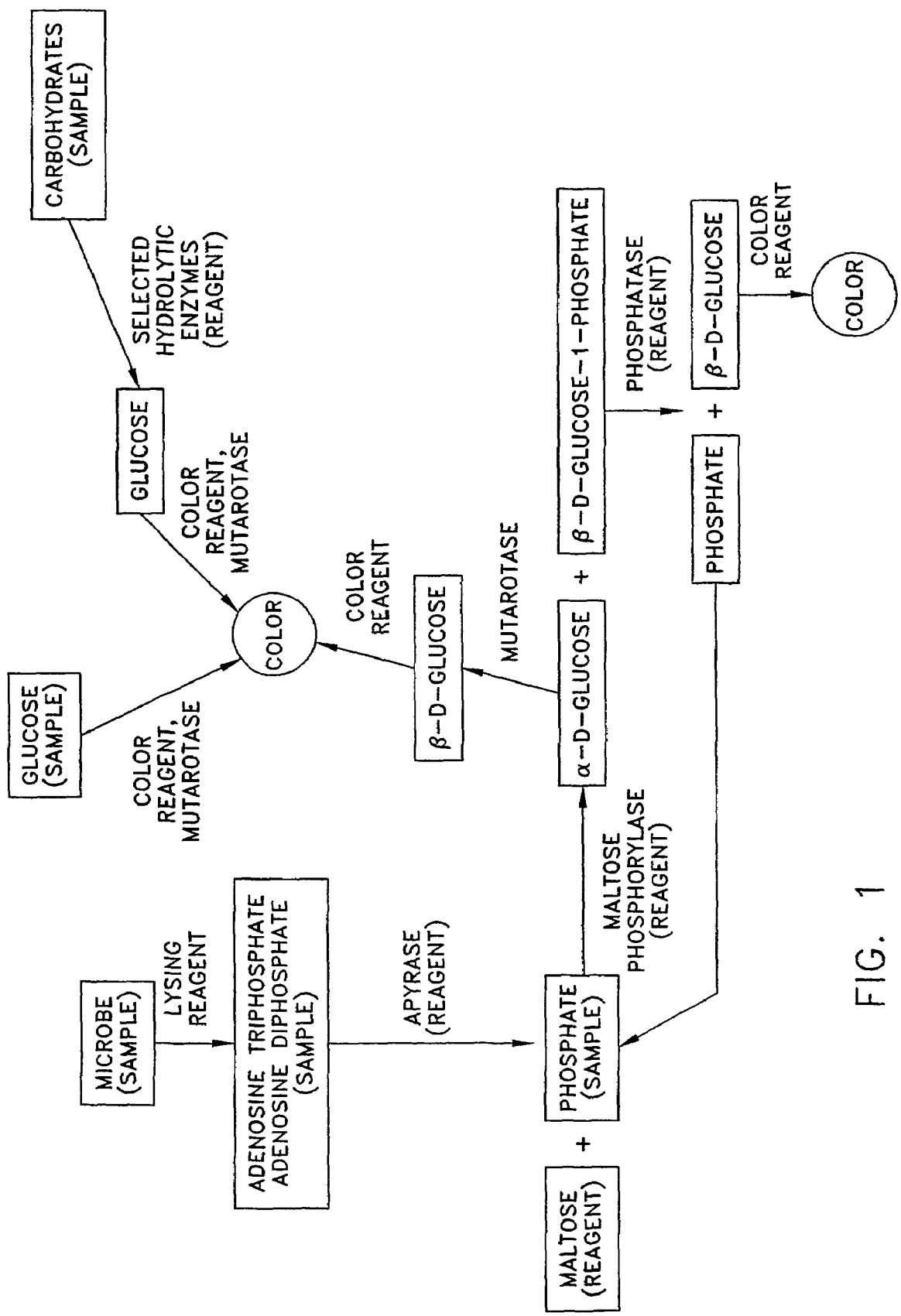
FIG. 1 is a reaction scheme that is utilized for general hygiene monitoring.

The purpose of the rapid, one-step, assay test for hygiene monitoring is to detect rapidly (within one minute, preferably within 2 minutes) the presence of biological material as an indicator of sanitation and cleanliness. The two materials detected, within the same single service test, are glucose and phosphate. Glucose is detected directly. Phosphate is detected indirectly by the reaction of maltose phosphorylase with maltose to produce glucose.

Enzymes are added to the assay system to increase the assay spectrum by converting biological material to glucose or phosphate. Materials are stablilized, purified to remove phosphate, adenosine triphosphate (ATP), adenosine diphosphate (ADP), glucose, and glucosidase, and placed in a POCKETSWAB® or lateral-flow test strip format, both of which are single assay formats that permit an easy testing format and rapid analysis.

Inorganic phosphate is ubiquitous in nature. It is involved in energy metabolism and activation reactions in plants, animals, and microorganisms. Inorganic phosphate is an important component in many compounds and, as a major biological mineral, it is present alone in significant amounts. Phosphates are used extensively in the food industry, including also as additives in dairy products, cereals, meats, and soft drinks.

Similarly, carbohydrates, including sugars, are present in and on biological materials in significant amounts. For example, glucose is present in blood, fruits, and honey. Acid phosphatase is endogenous to certain animal tissue, and alkaline phosphatase is present in feces. The detection of phosphate, phosphatase, and glucose are markers of contamination. Other carbohydrates, including sugars, can be converted to glucose for detection. For example, lactose, a milk sugar, can be converted to glucose by β-galactosidase. Sucrose, which is used in processed foods and is found in cane sugar, fruits, and as invert sugar in processed foods, can be converted to glucose by sucrase or invertase.

The test utilizes several reaction pathways for the detection of biological material. The primary detection pathway uses maltose and maltose phosphorylase for the detection of phosphate. Phosphate present in the sample reacts with maltose and maltose phosphorylase to convert maltose into glucose and glucose-1-phosphate. The glucose formed is detected colorimetrically by methods well known in the art. The test also uses additional pathways to increase sensitivity. These additional pathways result in increased formation of either or both phosphate and glucose.

The test strip consists of nitrocellulose adhesively bound to a polystyrene backing, with one end having a sample pad absorbent area in fluid-flow contact with the nitrocellulose, and the other end having optionally attached to it, or incorporated into it, a container of a surface-wetting reagent. The container of surface-wetting agent can also be incorporated into the test strip packaging. The wetting reagent container can be in the form of, for example, a burstable pouch or peel-top container.

Within the test strip are reagents providing biochemical pathways for the conversion of common surface biological material to glucose or phosphate. Also located within the test strip are reagents for the calorimetric detection of glucose. All reagents are stabilized, purified to remove phosphate, ATP, ADP, glucose, and glucosidase, and either sprayed onto the lateral-flow test strip, incorporated into the absorbent pad, or mixed with wetting solution.

Also within the test strip, preferably at the end opposite the sample-absorbing end, there can be included a positive control area for use in comparison of the color change and to confirm that adequate sample flow occurred.

Various embodiments comprise reagents for three (optionally, four or five or more) separate pathways.

Pathway 1:

A. Using apyrase to convert ADP and ATP to phosphate; and

B. Using maltose phosphorylase to convert phosphate and maltose to glucose and glucose-1-phosphate.

Phosphate can exist in free form on a surface or as phosphate in ADP or ATP. The phosphate component of ATP/ADP can be liberated by apyrase. Apyrase contains ADPase and ATPase activity and, therefore, converts ATP or ADP to AMP and phosphate. The liberated phosphate and the endogenous phosphate are detected by the reaction of maltose with phosphate and maltose phosphorylase to produce glucose and glucose-1-phosphate. The glucose formed from the reaction of maltose with phosphate in the presence of maltose phosphorylase is detected as described in Pathway 3.

Pathway 2: Sugar Conversion to Glucose

Carbohydrates, including sugars, are present in and on biological materials in significant amounts. Many sugars can be converted to glucose for detection. For example, lactose, a milk sugar, can be converted to glucose by β-galactosidase. Sucrose, which is used in processed foods and is found in cane sugar, fruits, and as invert sugar in processed foods, can be converted to glucose by sucrase or invertase. The glucose formed by these reactions is detected as described in Pathway 3.

Pathway 3: Detection of Glucose

Reactions for the colorimetric detection of glucose are well known in the art. For example, β-D-glucose+$O_2$+$H_2O$ are converted by glucose oxidase to D-glucono-δ-lactone+$H_2O_2$. The hydrogen peroxide formed from the above reaction, combined with a peroxidase enzyme, such as horseradish peroxidase, converts a colorless substrate to a dye that is readily visible. A mutarotase may be included to enhance sensitivity by converting α-D-glucose associated with phosphorylation to β-D-glucose to react with the glucose oxidase.

Other Pathways:

A: Glucose-phosphate, such as glucose-1-phosphate formed by the reaction of maltose with phosphate and maltose phosphorylase, Pathway 1 B, or present otherwise in the sample, can be cleaved by phosphatase, for example, acid phosphatase, to produce both glucose and phosphate. Providing phosphatase as a test reagent, therefore, increases test sensitivity.

B: In certain environments, detection of phosphatase is important. Glucose-phosphate, for example, glucose-6-phosphate, can be provide as a test reagent for detection of phosphatase. If phosphatase is present in the sample, glucose-6-phosphate will be cleaved to produce glucose and phosphate for detection, as previously described.

Sensitivity

The following test results compare Charm Sciences, Inc.'s POCKETSWAB®, read on both Charm Sciences, Inc.'s LUMINATOR® and Firefly instruments, with this new one-step assay test, referred to as the VERICLEEN™ test (VERICLEEN™ is a trademark of Charm Sciences, Inc. of Lawrence, Mass.). The VERICLEEN™ swabs, which do not require a reader, compares favorably to the POCKETSWAB®, which requires a reader.

Test Ingredients

Test results described herein were generated using the following test ingredients incorporated into a single-service device similar to that described in U.S. Pat. No. 5,827,675, issued Oct. 27, 1998; and U.S. Pat. No. 5,965,453, issued Oct. 12, 1999 (TEST APPARATUS, SYSTEM AND METHOD FOR THE DETECTION OF TEST SAMPLES). It should be noted that prior to use, all reagents must be verified as free from glucose and phosphate contamination; otherwise, they must be purified using dialysis, de-salting, enzyme treatment, or other appropriate method.

EXAMPLE 1

Substrate composition:

Maltose (approximately 470 µg)

EHSPT (approximately 125 µg)

4-aminoantipyrine (approximately 62 µg)

All 3 reagents are first lyophilized separately in a stabilizing buffer, then optionally combined in a cellulose tablet formation.

EXAMPLE 2

Enzyme composition:

Maltose phosphorylase (approximately 1.5 units)

Horseradish peroxidase (approximately 5 units)

Glucose oxidase (approximately 12.5 units)

β-galactosidase (approximately 1 unit)

Apyrase (approximately 1.7 units)

All enzymes are lyophilized separately, then optionally combined in a cellulose tablet formulation.

EXAMPLE 3

Liquid niblet:

Sterile deionized water with 1 mM $CaCl_2$ and preservative.

Comparison of Charm Sciences, Inc.'s

VERICLEEN™ vs. POCKETSWAB®

Sample Preparation:

Solids: includes fruits, vegetables, ice cream, meats, bread, and flour

20% extract: 2 grams food +8 mL deionized water; pound with tissue masher for 30 seconds; let solids settle prepare all dilutions from the 20% extract in deionized water Liquids: includes orange juice, milk, eggs, and soda product "as is" is 100% extract prepare all dilutions from the 100% extract in deionized water Assay:

1. Inject 50 µL extract directly into swab;
2. Activate swab device by twisting;
3. For PKS assay, count immediately on the Firefly analyzer; and
4. For VERICLEEN™, set time counting up; note time when purple color appears.

Blank testing:

run swab devices without removing swab

| POCKETSWAB® Blanks | VERICLEEN™ Blanks |
|---|---|
| Firefly RLU Reading | |
| 0 | color development after 6 minutes |
| 0 | color development after 5.5 minutes |
| 0 | color development after 6 minutes |

TABLE 1

| Fruits and Vegtables | Extract Concentration | POCKETSWAB® Firefly RLU Reading | VERICLEEN™ Result (DNR = did not run) |
|---|---|---|---|
| Celery | 20% | 265187 | DNR |
| Celery | 5% | 74256 | DNR |
| Celery | 1% | 19918 | DNR |
| Celery | 0.1% | 2943 | purple in 30 seconds |
| Cucumber | 20% | 270914 | DNR |
| Cucumber | 5% | 57434 | DNR |
| Cucumber | 1% | 41790 | purple in 20 seconds |
| Cucumber | 0.1% | 2965 | purple in 2.5 seconds |
| Carrot | 20% | 311245 | purple in 15 seconds |
| Carrot | 5% | 67449 | purple in 30 seconds |
| Carrot | 1% | 10318 | DNR |
| Carrot | 0.1% | 205 | purple in 60 seconds |
| Lettuce | 20% | 130230 | DNR |
| Lettuce | 5% | 30816 | DNR |

TABLE 1-continued

| Fruits and Vegtables | Extract Concentration | POCKETSWAB ® Firefly RLU Reading | VERICLEEN ™ Result (DNR = did not run) |
|---|---|---|---|
| Lettuce | 1% | 4689 | purple in 30 seconds |
| Lettuce | 0.1% | 0 | purple in 2 minutes |
| Apple | 20% | 735903 | DNR |
| Apple | 5% | 162292 | DNR |
| Apple | 1% | 60205 | DNR |
| Apple | 0.1% | 2747 | purple in 15 seconds |
| Orange (fresh squeezed juice) | 5% | 3108565 | DNR |
| Orange (fresh squeezed juice) | 1% | 872245 | DNR |
| Orange (fresh squeezed juice) | 0.1% | 120521 | DNR |
| Orange (fresh squeezed juice) | 0.01% | 23387 | purple in 40 seconds |
| Orange Juice (pasteurized) | 5% | 3264303 | DNR |
| Orange Juice (pasteurized) | 1% | 819838 | DNR |
| Orange Juice (pasteurized) | 0.1% | 145470 | DNR |
| Orange Juice (pasteurized) | 0.01% | 4961 | purple in 60 seconds |

TABLE 2

| Dairy Products | Extract Concentration | POCKETSWAB ® Firefly RLU Reading | VERICLEEN ™ Result (DNR = did not run) |
|---|---|---|---|
| Raw Milk | 5% | 50081 | DNR |
| Raw Milk | 1% | 29572 | DNR |
| Raw Milk | 0.1% | 13732 | purple in 45 seconds |
| Raw Milk | 0.01% | 1547 | purple in 4 minutes |
| Pasteurized Milk | 50% | 213870 | purple in 45 seconds |
| Pasteurized Milk | 5% | 35594 | pale purple in 4 minutes |
| Pasteurized Milk | 1% | 6074 | DNR |
| Pasteurized Milk | 0.1% | 0 | DNR |
| Whole egg beaten | 5% | 2714 | DNR |
| Whole egg beaten | 1% | 0 | DNR |
| Whole egg beaten | 0.1% | 0 | purple in 30 seconds |
| Whole egg beaten | 0.01% | 0 | purple in 45 seconds |
| Soft serve ice cream | 20% | 47594 | purple in 30 seconds |
| Soft serve ice cream | 5% | 10241 | purple in 45 seconds |
| Soft serve ice cream | 1% | 0 | purple in 2 minutes |
| Soft serve ice cream | 0.1% | 0 | purple in 3.5 minutes |

TABLE 3

| Meats | Extract Concentration | POCKETSWAB ® Firefly RLU Reading | VERICLEEN ™ Result (DNR = did not run) |
|---|---|---|---|
| Raw Ground Beef | 20% | 279489 | DNR |
| Raw Ground Beef | 5% | 31154 | DNR |
| Raw Ground Beef | 1% | 3543 | DNR |
| Raw Ground Beef | 0.1% | 0 | purple in 20 seconds |
| Cooked Ground Beef | 20% | 831281 | DNR |
| Cooked Ground Beef | 5% | 3629780 | DNR |
| Cooked Ground Beef | 1% | 4773347 | purple in 30 seconds |
| Cooked Ground Beef | 0.1% | 1305347 | purple in 4 minutes |
| Raw chicken breast | 20% | 457994 | DNR |
| Raw chicken breast | 5% | 43972 | DNR |
| Raw chicken breast | 1% | 0 | purple in 60 seconds |
| Raw chicken breast | 0.1% | 0 | purple in 1.5 seconds |
| Cooked chicken breast | 20% | 694045 | DNR |
| Cooked chicken breast | 5% | 3825860 | purple in 45 seconds |
| Cooked chicken breast | 1% | 4457393 | Negative at 4 minutes |
| Cooked chicken breast | 0.1% | 1730583 | DNR |

TABLE 4

| Grains | Extract Concentration | POCKETSWAB ® Firefly RLU Reading | VERICLEEN ™ Result (DNR = did not run) |
|---|---|---|---|
| White Flour | 20% | | DNR |
| White flour | 5% | | purple in 20 seconds |
| White flour | 1% | | purple in 30 seconds |
| White flour | 0.1% | | purple in 2 minutes |
| White bread | 20% | | DNR |
| White bread | 5% | | DNR |
| White bread | 1% | | DNR |
| White bread | 0.1% | | purple in 50 seconds |

TABLE 5

| Soft Drinks | Extract Concentration | POCKETSWAB ® Firefly RLU Reading | VERICLEEN ™ Result (DNR = did not run) |
|---|---|---|---|
| Coke | 5% | 0 | DNR |
| Coke | 1% | | purple in 30 seconds |
| Coke | 0.1% | | purple in 60 seconds |
| Coke | 0.01% | | pale purple at 4 minutes |
| Sprite | 5% | 0 | purple in 20 seconds |
| Sprite | 1% | | DNR |
| Sprite | 0.1% | | purple in 60 seconds |
| Sprite | 0.01% | | DNR |

The invention also comprises a method for increasing the above-described hygiene monitoring test sensitivity to phosphate, through a cycling reaction. Phosphatase, for example acid phosphatase, which is included as a test reagent and may be present in the sample, cleaves bound phosphate, such as glucose-1-phosphate and glucose-6-phosphate into its component, glucose and phosphate which both will be detected within the assay system. Glucose-1-phosphate and glucose-6-phosphate may be from the sample and also, in the case of glucose-1-phosphate, generated as a reaction product of the carbohydrate substrate with phosphate in the presence of an appropriate enzyme as previously described. The reaction product glucose-1-phosphate is broken down by phosphatase to produce more glucose for the color change reaction and more phosphate to combine with the carbohydrate substrate as previously described.

The invention also comprises a way to release phosphate and glucose from various commonly found surface contaminants such as adenosine triphosphate (ATP), adenosine diphosphate (ADP), biofilms, carbohydrates, microbes, and phosphatase. A method for releasing phosphate and glucose from such contaminants includes using enzymes such as phosphatase, for example apyrase and glucose phosphatase, and enzymes, such as hydrolytic enzymes, to breakdown carbohydrates comprised of more than one saccharide (complex carbohydrates) to release the glucose component, for example the breakdown of lactose by β-galactosidase, the breakdown of sucrose by invertase and the breakdown of starch by amylase. A method for releasing various molecules such as ATP, ADP and glucose from microbes includes the use of lysing reagents. A mutarotase may be included to enhance sensitivity by converting α-D-glucose associated with phosphorylation to β-D-glucose to react with the glucose oxidase.

The presence of acid phosphatase on a surface is indicative of contamination with certain animal tissue. A separate embodiment of the invention includes additional way to detect phosphatase. Such methods may be included within the assay system in circumstances where detection of phosphatase is relatively more important than increasing test sensitivity to phosphate, for example when detection of animal tissue, such as muscle or blood, is relatively more important compared to the general increase sensitivity to phosphate. However, the above-described methods for increasing test sensitivity to phosphate, by providing phosphatase as a reagent, cannot practically be combined with the methods for detecting phosphatase in a sample. Methods for detecting phosphatase include providing glucose-6-phosphate or glucose-1-phosphate as a test reagent. Phosphatase present in the sample will cleave, for example glucose-6-phosphate, into is components glucose and phosphate.

The invention involves a method for the rapid, colorimetric determination of hygiene monitoring of surface contamination, which method comprises: adding a phosphorylase enzyme and carbohydrate substrate to a sample containing phosphate to create a reaction product of free glucose and phosphate bound to a saccharide; cleaving free phosphate from said bound phosphate; cleaving free glucose from complex carbohydrates; releasing or extracting intracellular phosphate; and changing the interconversion of α-D-glucose to β-D-glucose, wherein free glucose is detected in a colorimetric reaction as a measure of surface contamination.

The invention also involves a method for the rapid, colorimetric determination of hygiene monitoring of surface contamination including contamination with phosphate and phosphatase, which method comprises: adding a phosphorylase enzyme and a carbohydrate substrate to a sample containing phosphate to create a reaction product of free glucose and phosphate bound to a saccharide; cleaving free phosphate from bound phosphate; cleaving free glucose from complex carbohydrates; releasing intracellular phosphate; and catalyzing the interconversion of α-D-glucose to β-D-glucose, wherein free glucose is detected in a colorimetric reaction as a measure of surface contamination.

The invention also comprises a device for rapid, colorimetric hygiene monitoring, which test device comprises: a capillary-flow test strip having two ends, the test strip includes at a first end, a liquid sample absorbing material; reagents for conversion of biological material to glucose, such as by providing multiple biochemical pathways; and reagents for the colorimetric detection of glucose, wherein a liquid sample from a material is absorbed onto the first end and flows by capillary action to contact reagents providing biochemical pathways for conversion of biological material to glucose and colorimetric detection of glucose.

The invention also comprises a device for rapid, colorimetric hygiene monitoring having one or more reaction zones, included on or in a capillary membrane, comprising reagents for conversion of biological materials to glucose and phosphate and reagents which, in the presence of phosphate and an appropriate enzyme, convert certain biological materials to glucose; and reagents for the colorimetric detection of glucose, wherein a liquid sample from a material is absorbed onto the first end and flows by capillary action through the test strip containing reagents, which produces a visually detectable readout in the presence of glucose.

The invention also comprises a device for hygiene monitoring, by detecting biological material in a test sample from or on a material, which test device comprises: a swab to collect the test sample and a niblet comprising separate, swab-puncturable, membrane compartments for one or more reagents and a solution; an enzyme reagent composition, preferably in tablet form, comprising glucose oxidase, horseradish peroxidase, maltose phosphorylase, apyrase, β-galactosidase and phosphatase; a substrate reagent composition, preferably in tablet form, comprising 4-aminoantipyrene, mutarotase, EHSPT (the Trinder's reagent TOOS), and maltose; and a liquid reagent comprising a buffering solution and lysing solution, wherein the sample is contacted sequentially with the liquid reagent, enzyme reagent, and substrate reagent and a color change or lack thereof is observed as a measure of hygiene.

The test apparatus of certain embodiments of the invention is in the format of the POCKETSWAB®, which is described in U.S. Pat. No. 5,965,453, issued Oct. 12, 1999 (TEST APPARATUS, SYSTEM AND METHOD FOR THE DETECTION OF TEST SAMPLES); U.S. Pat. No. 5,985,675, issued Nov. 16, 1999 (TEST DEVICE FOR DETECTION OF AN ANALYTE); and U.S. Pat. No. 6,180,395, issued Jan. 30, 2001 (REAGENT CHAMBER FOR TEST APPARATUS AND TEST APPARATUS), which are incorporated herein in their entirety. In these embodiments, the apparatus incorporates a foam-tipped, or other absorbent-type swab or wand for sample uptake from the surface to be monitored. The swab may be premoistened with a wetting solution.

After sample uptake onto the swab, the swab is used to puncture a series of "niblets" releasing and activating the necessary reagents. The term "niblet" refers to a reagent chamber in the form of a cylinder containing reagents and sealed on both ends with a probe puncturable membrane.

In certain embodiments, the first niblet to contact the swab includes cofactors and buffering compounds to optimize subsequent reactions and antimicrobial or antifungal substance to prevent contamination. In other embodiments, the first niblet may additionally contain bacterial lysing reagents.

After the swab is contacted with the first reagent niblet, the swab is contacted with the material in the second niblet by, preferably, puncturing the membranes separating the first and second niblet, thereby causing reagents from the first niblet to flow into and mix with reagents in the second niblet. The second niblet contains one or more reagents, preferably tablets, containing enzymes, substrates, and biochemicals. Certain embodiments include two tablets in the second niblet, generally referred to as the "substrate tablet" and the "enzyme tablet."

In some embodiments, the substrate reagent composition includes maltose, glucose-phosphates, such as glucose-1-phosphate or glucose-6-phosphate, TOOS and 4-aminoantipyrine, and the enzyme reagent includes maltose phosphorylase, horseradish peroxidase, glucose oxidase, mutarotase, β-galactosidase and apyrase. In other embodiments, enzymes for converting other carbohydrates to glucose, for example, amylase, sucrase (invertase) may be included.

In another embodiment, glucose-6-phosphate is removed from the substrate reagent. Such an embodiment will be less sensitive to sample phosphatase. Instead, phosphatase is added to the enzyme reagent or substrate reagent. The added phosphatase will cleave the glucose1-phosphate reaction product of maltose and phosphate to produce additional phosphate and glucose, thereby enhancing test sensitivity to phosphate through the additional cycling of the phosphate group, from the glucose-1-phosphate, to be combined with maltose and maltose phosphorylase. It will be appreciated that although the reagents of particular embodiments are described as "tablets" or "liquid," the reagents can be used in, and applied to, the test device in a variety of forms, which forms are prepared separately or in combination, including solid, liquid, powder, freeze-dried, emulsion, suspension, tablet, or any other form known to those skilled in the art.

The test apparatus of certain other embodiments of the invention is in the format of a capillary-flow test strip. The strip consists of a capillary-flow capillary membrane, for example, nitrocellulose membrane, adhesively bound to a backing, for example a polystyrene backing, with one end having a sample pad absorbent area in fluid flow contact with the membrane. Optionally, at the sample pad end, or the other end, the strip could have attached, or incorporated into the packaging, a container of a surface wetting reagent. The container of surface-wetting agent may include a wetting solution. The wetting solution container can be in the form of, for example, a burstable pouch or peel-top container within the test strip packaging. Alternatively, the surface-wetting solution can be included in a bulk container, for example, a squeezable, plastic, dispenser bottle or spray bottle, which is attached at the end opposite the dispensing end, to a container within which capillary-flow strips are placed. The wetting solution should, optimally, be pH neutral, food compatible and non-interfering. The capillary-flow strip container is formed of a light-blocking material to protect the test strips. Applied to the test strip capillary membrane are reagents for the production of glucose and phosphate from common surface biological material and reagents for the colorimetric detection of glucose.

In one example of the capillary-flow strip, reagents are provided in two zones. The two reagent zones are applied to the membrane portion of the test strip in fluid flow contact with the absorbent pad. Optionally, the reagents can be applied by spraying onto the strip. In one embodiment, the first reagent zone contains a carbohydrate substrate, for example, maltose and glucose-6-phosphate. In an alternative embodiment, the first reagent zone contains the carbohydrate substrate and a phosphatase, for example, acid phosphatase. The second reagent zone contains reagents for the colorimetric detection of glucose, for example, TOOS, glucose oxidase, mutarotase, horseradish peroxidase and 4-aminoantipyrene. Also included within the second reagent zone are enzymes, such as maltose phosphorylase and apyrase and one or more hydrolytic enzymes, such as β-galactosidase.

The reagents in this device are able to flow in the membrane reacting with the sample and each other. Sufficient capillary-flow space is included beyond the second reagent zone for color reagents to change color in the presence of a target material and provide an easily read, visible result. The space beyond the second reagent zone is sufficiently small to create a defined area for color change to occur. Color change begins at the end of the capillary membrane and spreads back. Providing space between the second reagent zone and the end of the capillary membrane permits a wider, more visible line to develop. At the end of the capillary membrane is an air gap to prevent reagent flow beyond the end of said membrane, a wetting solution for solubilizing surface food residue and penetrating biofilm.

All reagents are stabilized, purified to remove phosphates, glucose and maltose degrading enzymes, for example, glucosidase, and either sprayed onto the capillary-flow membrane or incorporated into the absorbent pad.

The test apparatus system and method will be described for the purposes of illustration only in connection with a series of illustrative test apparatus and test method employing various test apparatus. However, it is recognized that those persons skilled in the art may make various modifications, changes, additions, and improvements to the test apparatus, system and methods without departing from the spirit and scope of the invention.

EXAMPLE 4

The lateral or capillary-flow strip consists of a nitrocellulose membrane onto which two regions, zones, or lines of reagents have been applied using appropriate manufacturing equipment, such as that made by BioDot, Inc. Optionally, the membrane is overlapped with an absorbent cellulose paper pad. One region consists of all enzymes needed for the color reaction, the enzymes for release of phosphate and glucose, plus the two substrates necessary for color development. Prior to use, all enzymes must be purified to remove any sugar or phosphate contamination, for example, by desalting. The second line contains a preparation of glucose-free maltose and purified acid phosphatase. The nitrocellulose is mounted onto a polystyrene backing material and, optionally, packaged into a plastic, blister-type device. If packaged into a blister-type device the device, optionally, contains a bubble to which surface wetting agent is added; the bubble may be sealed with peelable foil.

The reagents applied to the capillary membrane are the same as those used as reagents or tablets for the swab-type assay. However, the amount of each component required per test is significantly lower for all reagents. The approximate amount of each reagent and its corresponding amount used in the swab test are listed in Table 6, in an embodiment including glucose-6-phosphate and Table 7 in an embodiment including acid phosphatase.

Results generated with the embodiment described in Table 6 are listed in Appendix 1.

TABLE 6

| Reagent | Amount per Test in Capillary-Flow Membrane | Amount per Test in Swab Test |
| --- | --- | --- |
| TOOS | 930 ng | 125 mg |
| 4-aminoantipyrine | 460 ng | 63 mg |
| Maltose | 2 mg | 470 mg |
| Maltose phosphorylase | 0.06 units | 1.5 units |
| Glucose oxidase | 0.5 units | 12.5 units |
| Horseradish peroxidase | 0.2 units | 5 units |
| β-galactosidase | 0.04 units | 0.8 units |
| Glucose-6-phosphate | 10 mg | 100 mg |
| Apyrase | 0.2 units | 1.5 units |

Appendix 1

Test Data

I. Assay in Which Solution of Food Product is Allowed to Air Dry onto Countertop then Rehydrated with Wetting Solution and Wiped with Test Strip

| Food | Concentration | Time to Color Change (s) |
| --- | --- | --- |
| Beef | 2% | 16, 15 |
| Chicken | 5% | 10, 7 |
| Fish | 5% | 20, 23 |
| Ketchup | 1% | 3, 2 |
| Milk | 10% | 35, 37 |
| Orange juice | 2% | 4, 3 |
| Egg | 2% | 4, 5 |

II. Assay in Which Wet Solution of Food Product is Wiped from Plastic Surface with Test Strip

| Food | Concentration | Time to Color Change (s) |
| --- | --- | --- |
| Beef | 2% | 8, 10 |
| Chicken | 5% | 8, 7 |
| Fish | 5% | 9, 8 |
| Ketchup | 1% | 2, 2 |
| Milk | 10% | 30, 32 |
| Orange juice | 2% | 2, 3 |
| Egg | 2% | 5, 5 |

TABLE 7

| Component | Amount per Test in Capillary-Flow Membrane | Amount per Test in Swab Test |
| --- | --- | --- |
| Glucose oxidase | 0.7 units | 12.5 units |
| Horseradish peroxidase | 0.3 units | 5 units |
| β-galactosidase | 0.06 units | 1 units |
| Maltose phosphorylase | 0.09 units | 3 units |
| Apyrase | 0.3 units | 5 units |
| Acid phosphatase | 0.01 units | 0.1 units |
| Maltose | 4 mg | 1400 mg |
| 4-aminoantipyrene | 700 ng | 63 mg |
| N-ethyl-N-(2-hydroxy-3-sulfopropyl)-m-toluidine | 1400 ng | 125 mg |

Materials are stabilized, purified to remove phosphate, ATP, ADP, glucose and glucosidase, and placed in a POCK-ETSWAB® or capillary-flow membrane format, both of which are single assay formats that permit an easy testing and rapid analysis.

FIG. 1 illustrates the general use reaction scheme of the invention, which is particularly useful when testing for a wide range of contaminants. Maltose reacts with phosphate from the sample in the presence of maltose phosphorylase to form α-D-glucose and β-D-glucose-1-phosphate. β-D-glucose forms color when combined with certain well-known reagents. α-D-glucose naturally converts to β-D-glucose. The rate of natural conversion can be enhanced by mutarotase. The β-D-glucose-1-phosphate in the presence of acid phosphatase (as a test reagent) is broken down into phosphate and β-D-glucose (Phosphatase from the sample will also break down β-D-glucose-1-phosphate.). The glucose enters into the color reaction amplifying the color from the first glucose, and the phosphate reacts with more maltose (a test reagent) to generate more glucose and, ultimately, more phosphate and more color until the maltose reagent is depleted, or the reaction is otherwise inhibited. The above-described cycling of phosphate produces a sensitive test for phosphate in the sample. The reaction scheme also includes examples of conversion of common biological material to glucose and phosphate. Lysing reagents release ATP and ADP from microbes and apyrase cleaves the phosphate. Carbohydrates are hydrolized to release glucose for detection.

Figure 2:
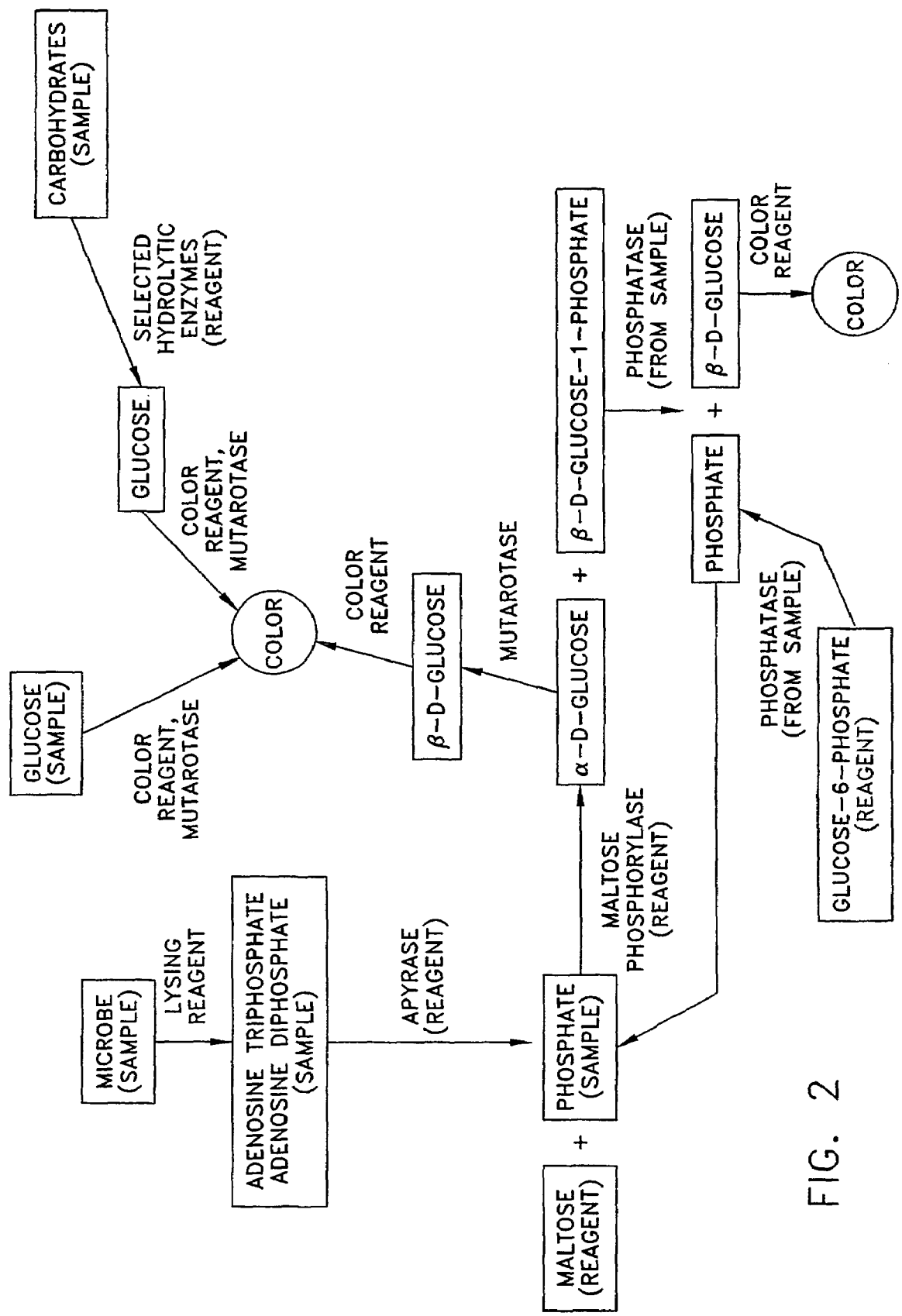
FIG. 2 is a reaction scheme that may be utilized when sensitivity to animal tissue is of particular importance.

FIG. 2 illustrates the reaction scheme particularly useful for detecting contamination from raw or partially-cooked meat products. Glucose-6-phosphate (or alternatively glucose-1-phosphate) is added as a reagent to include an additional source of phosphate and glucose when acid phosphatase is present in the sample. In the embodiment represented by said reaction scheme, acid phosphatase is not a reagent and is, instead, supplied from the sample. If acid phosphatase is not present, the glucose-6-phosphate does not enter the reaction, and only phosphate from the sample generates glucose. Color is generated by the glucose.

FIGS. 3A & B illustrate the invention in the format of the swab-type device. In use of the swab-type device of the invention, the swab 1 is removed from the body 3, by gripping the swab handle 2, and a 4"×4" surface, for example, a food contact surface, is swabbed using the pre-moistened swab 1. The swab 1 is then reinserted into the body 3 and screwed longitudinally through the covering 9 of the microtube test unit 4 and through the covering 10 of the liquid reagent niblet 5 and into the tablet niblet 6 containing an enzyme tablet 7 and a substrate tablet 8. The liquid released to the bottom of the microtube test unit 4 turns purple within 60 seconds if the surface is "dirty," for example, it has food residue contamination.

Figure 4:
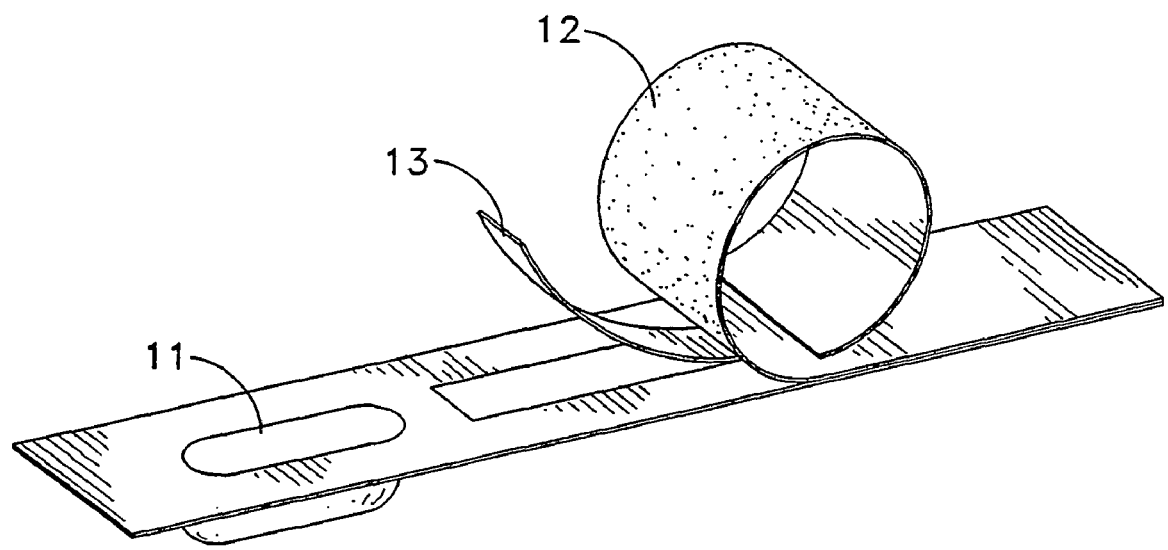
FIG. 4 is a side perspective view of the VERICLEEN™ test strip within the optional blister package with the package covering pulled partially back to expose the wetting solution and capillary-flow test strip.

FIG. 4 illustrates the invention in the capillary-flow strip-type device packaged within a blister package. In use of the capillary-flow strip test-type device of the invention, the blister package cover 12 is peeled back, and the surface-wetting solution is released from the container 11 onto the surface to be monitored. The user continues to peel back the covering 12 to expose the test strip 13.

Figure 5:
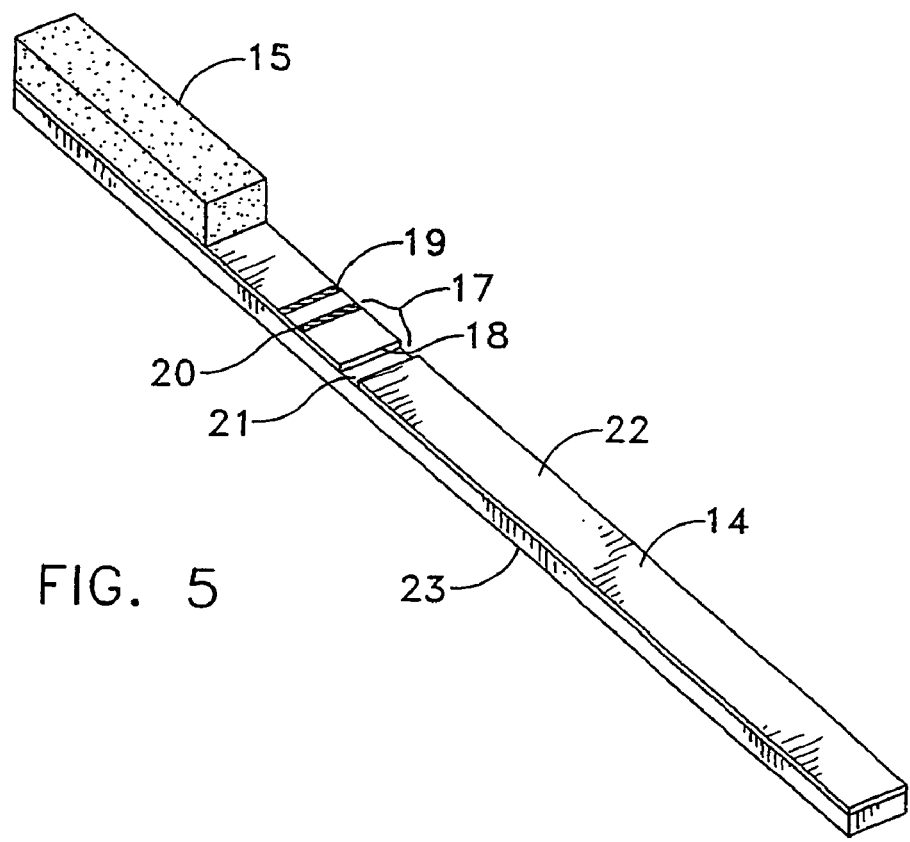
FIG. 5 is a side perspective view of the VERICLEEN™ test strip including a space or gap to prevent diffusion of color reagents.

FIG. 5 is a side perspective view of the VERICLEEN™ test strip. While handling area 14 the absorbent pad 15 is used to swab the surface to be monitored. The sample is absorbed onto sample pad 15 and flows by capillary action through the first reagent zone 19, to the second reagent zone 20 (Reagent zones 19 and 20 are depicted for illustration.). In the preferred embodiment, reagent zones 19 and 20 are slightly visible or invisible. Sample flow stops at the end of the capillary membrane 18. Positive results are reflected in color change zone 17. Color change begins to form at the end of the capillary membrane 18 and spreads back. A gap 21 is included sufficiently wide to prevent unwanted diffusion of color into the cover 22 of the backing 23, which cover 22 and backing 23 combined make up the handling area 14. Line development at the top of the capillary membrane, within approximately one minute, indicates presence of residue and need to clean. All valid tests will change color after approximately five minutes. Reagent zones 19 and 20 contain reagents depicted in the reaction scheme of either FIG. 1 or FIG. 2, depending on the requirements of the user.

Figure 6:
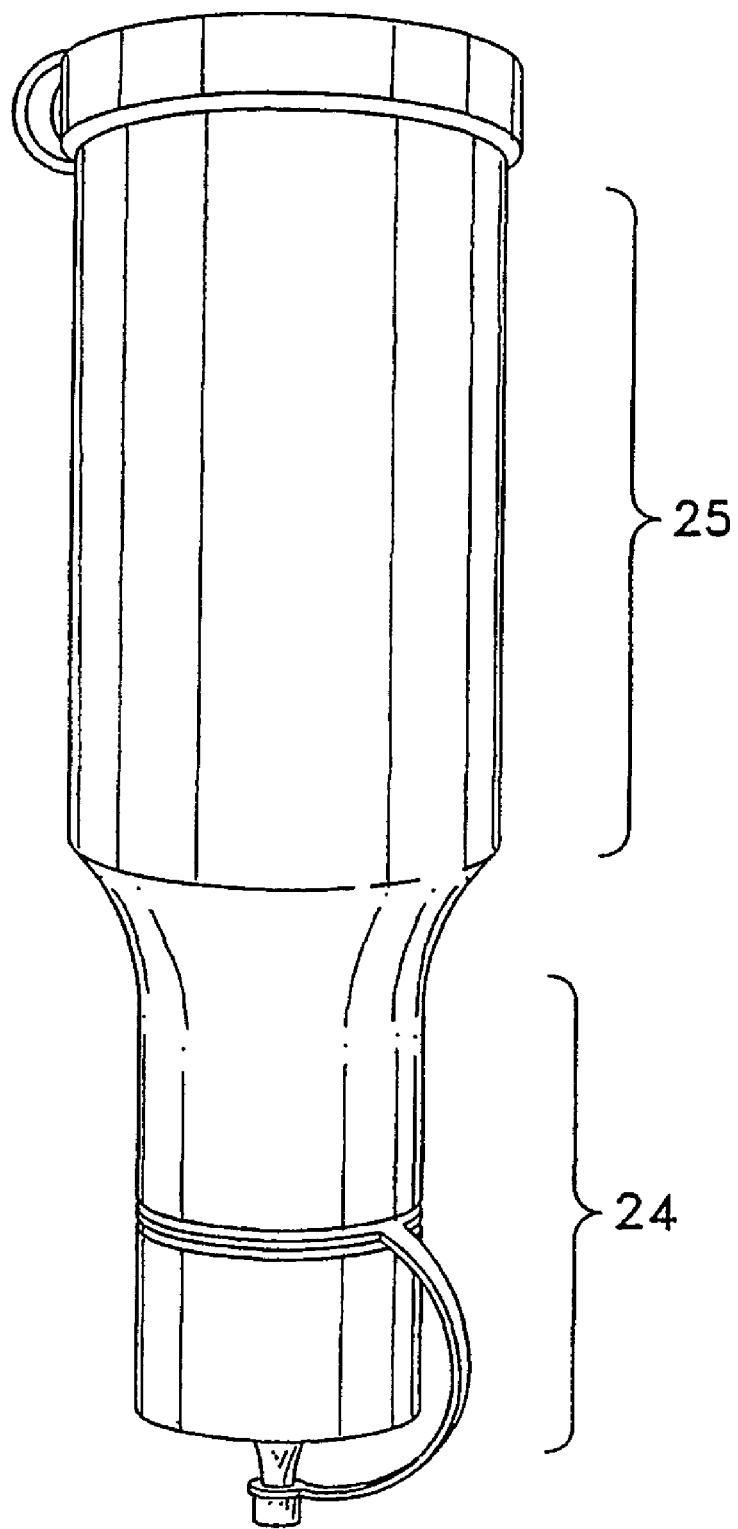
FIG. 6 is a side perspective view of the wetting-agent dispenser attached to a test strip container.

FIG. 6 is a side perspective view of the wetting-agent dispenser 24 attached to a light-blocking test strip container 25.

Figure 7:
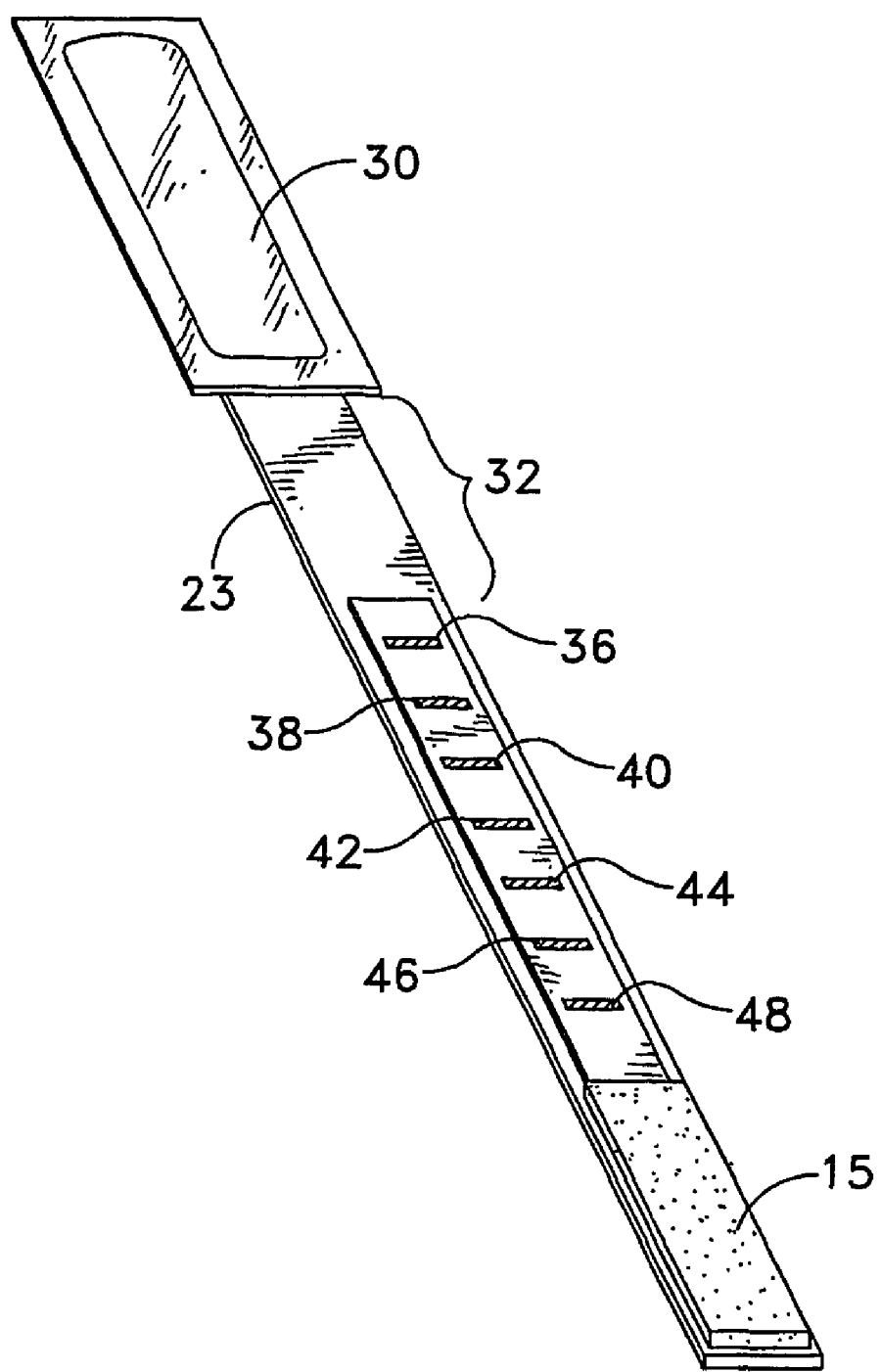
FIG. 7 is perspective view of the VERICLEEN™ test strip.

FIG. 7 illustrates an embodiment of the present invention containing a strip of nitrocellulose adhesively bound to a polystyrene support. Various reagents are sprayed and dried onto the nitrocellulose in a series of discreet zones. FIG. 7 contains seven such spaced-apart zones as follows:

Zone 1, 48, is comprised of apyrase and β-galactosidase. Apyrase cleaves any ATP/ADP liberating phosphate that will flow in the solution along the test strip to Zone 2. β-galactosidase converts lactose to glucose. Zone 2, 46, comprises maltose for reaction with phosphate, in the presence of the maltose phosphorylase to produce glucose. Zone 3, 44, is comprised of maltose phosphorylase. Zone 4, 42, is comprised of glucose oxidase for oxidation of glucose in a reaction that yields peroxide. Zone 5, 40, is comprised of EHSPT [N-ethyl-N-(2-hydroxy-3-sulfo-propyl)-n-toluidine], commonly referred to as TOOS; Zone 6, 30, is comprised of 4-aminoantipyrine; and Zone 7, 36, is comprised of horseradish peroxidase. Zones 5, 6, and 7, 40, 30, and 36, respectively comprise reagents which, in the presence of peroxide, produce a color precipitate which can be observed visually.

It is also possible to combine the seven zones described above into fewer zones, for example, three zones, containing multiple reagents per zone.

In operation, the wetting reagent is released onto the surface to be tested or absorbed onto the absorbent pad 15. Holding the strip at the finger-hold area 32, the sample pad 15 is used to swab the surface to be tested. Wetting the surface will suspend in the liquid some of the material to be detected. Material to be detected will be absorbed by the strip upon swabbing the wet surface. The liquid absorbed onto the strip will then flow laterally on the strip. Upon contact with a fluid-analyte, the reactants in the zones are resolubilized and react with the analyte(s) in the sample as described above. Color formation in the horseradish peroxidase 36 reaction zone indicates a positive sample, while no color indicates a clean sample.

What is claimed:

1. A method for rapidly monitoring the hygiene of an inanimate surface desired to be free of the presence of biological contamination, which method comprises the steps of:
   a) obtaining a sample from said surface;
   b) adding to said sample one or more enzymes, said one or more enzymes convert a carbohydrate that contains glucose to glucose; and
   c) detecting the presence or absence of glucose that has been enzymatically derived in step b from said sample, wherein the presence of said derived glucose from said sample is an indicator of said contamination on said surface and wherein less than 10 minutes elapses between step b and step c.

2. The method of claim 1, wherein said carbohydrate comprises one or more sugars.

3. The method of claim 1, wherein said carbohydrate comprises one or more complex carbohydrates.

4. The method of claim 1, wherein said carbohydrate comprises lactose.

5. The method of claim 1, wherein said enzyme comprises a hydrolytic enzyme.

6. The method of claim 5, wherein said enzyme comprises invertase.

7. The method of claim 5, wherein said enzyme comprises amylase.

8. The method of claim 5, wherein said enzyme comprises cellulase.

9. The method of claim 5, wherein said enzyme comprises β-galactosidase.

10. The method of claim 5, wherein said enzyme comprises sucrase.

11. The method of claim 1, wherein said detecting comprises adding to said sample a reagent for the colorimetric detection of said glucose.

12. The method of claim 11, wherein said reagent for the colorimetric detection of glucose comprises glucose oxidase.

13. The method of claim 11, wherein said reagent for the colorimetric detection of glucose comprises peroxidase.

14. The method of claim 1 comprising catalyzing the interconversion of α-D-glucose to β-D-glucose.

15. The method of claim 1, comprising using a swab to obtain the sample from said surface.

16. The method of claim 1, further comprising introducing the sample to the enzyme by applying the sample to a capillary-flow membrane, said membrane including the reagent.

17. The method of claim 1, further comprising adding to said sample a phosphorylase enzyme and a carbohydrate substrate to produce, in the presence of a phosphate in said sample, a reaction product of glucose and a phosphate-bound saccharide reaction product.

18. The method of claim 17, wherein the phosphorylase enzyme comprises maltose phosphorylase, and the carbohydrate substrate comprises maltose.

19. The method of claim 17, further comprising cleaving inorganic phosphate from an organic molecule containing phosphate.

20. The method of claim 17, wherein said cleaving comprises adding a phosphatase enzyme.

21. The method of claim 20, wherein the phosphate-bound saccharide reaction product is glucose-1-phosphate, and wherein the phosphatase enzyme cleaves phosphate from said glucose-1-phosphate.

22. The method of claim 20, wherein the phosphatase enzyme comprises apyrase.

23. The method of claim 20, wherein the phosphatase enzyme comprises acid phosphatase.

24. The method of claim 20, wherein the phosphatase enzyme comprises glucose phosphatase.

25. The method of claim 20, wherein said phosphatase enzyme comprises ATP hydrolase.

26. The method of claim 20, wherein the phosphatase enzyme comprises alkaline phosphatase.

27. The method of claim 1, further comprising releasing intracellular phosphate from a biological cell in said sample.

28. The method of claim 27, wherein said intracellular phosphate is released by a lysing reagent.

29. The method of claim 1, further comprising adding glucose-phosphate to a sample suspected of containing phosphatase, to produce a reaction product of glucose and phosphate.

30. The method of claim 29, wherein the glucose-phosphate is glucose-6-phosphate.

31. The method of claim 1, which method comprises introducing the sample to the reagents through one or more membrane-puncturable niblets.

32. The method of claim 1, which method comprises introducing the sample onto a capillary-flow membrane containing reagents for production of glucose and components for colorimetric detection of glucose.

33. The method of claim 32, wherein the reagents are not immobilized on the membrane and which method further comprises preventing flow of reagents after test completion so as to provide a defined area for detecting a color change reaction.

34. The method of claim 33, wherein a wetting agent is included in a sealed area within packaging of a test strip, and said wetting agent is applied to a surface sample prior to introducing said surface sample onto the test strip.

35. The method of claim 1, wherein said sample is a liquid obtained from a surface.

36. The method of claim 1, wherein the biological contamination is selected from the group consisting of food residues, microorganisms, and a combination of food residues and microorganisms.

37. The method of claim 1, wherein the biological contamination is selected from the group consisting of adenosine triphosphate, adenosine diphosphate, bioflims, carbohydrates, microbes, and phosphatase.

38. A method for monitoring the hygiene of a surface desired to be free of the presence of biological contamination, which method comprises the steps of:
   a) obtaining a sample from said surface;
   b) adding to said sample a hydrolytic enzyme for converting a carbohydrate that contains glucose to glucose, said hydrolytic enzyme comprising invertase; and
   c) detecting the presence or absence of glucose that has been enzymatically derived in step b from said sample, wherein the presence of said derived glucose from said sample is an indicator of said contamination on said surface.

39. The method of claim 38 wherein less than 10 minutes elapses between step b and step c.

40. The method of claim 38 wherein less than 5 minutes elapses between step b and step c.

41. The method of claim 38, further comprising adding to said sample a phosphorylase enzyme and a carbohydrate substrate to produce, in the presence of a phosphate in said sample, a reaction product of glucose and a phosphate-bound saccharide reaction product.

42. A method for monitoring the hygiene of a surface desired to be free of the presence of biological contamination, which method comprises the steps of:
   a) obtaining a sample from said surface;
   b) adding to said sample a hydrolytic enzyme for converting a carbohydrate that contains glucose to glucose, said hydrolytic enzyme comprising sucrase; and
   c) detecting the presence or absence of glucose that has been derived in step b from said sample, wherein the presence of the glucose derived in step b from said sample is an indicator of said contamination on said surface.

43. The method of claim 42 wherein less than 10 minutes elapses between step b and step c.

44. The method of claim 42 wherein less than 5 minutes elapses between step b and step c.

45. The method of claim 43, further comprising adding to said sample a phosphorylase enzyme and a carbohydrate substrate to produce, in the presence of a phosphate in said sample, a reaction product of glucose and a phosphate-bound saccharide reaction product.

46. A method for monitoring the hygiene of a surface desired to be free of the presence of biological contamination, which method comprises the steps of:
   a) obtaining a sample from said surface;
   b) adding to said sample a hydrolytic enzyme for converting a carbohydrate that contains glucose to glucose, said hydrolytic enzyme comprising beta-galactosidase; and
   c) detecting the presence or absence of glucose that has been derived in step b from said sample, wherein the presence of the glucose derived in step b from said sample is an indicator of said contamination on said surface.

47. The method of claim 46 wherein less than 10 minutes elapses between step b and step c.

48. The method of claim 46 wherein less than 5 minutes elapses between step b and step c.

49. The method of claim 46, further comprising adding to said sample a phosphorylase enzyme and a carbohydrate substrate to produce, in the presence of a phosphate in said sample, a reaction product of glucose and a phosphate-bound saccharide reaction product.

50. A method for monitoring the hygiene of a surface desired to be free of the presence of biological contamination, which method comprises the steps of:
   a) obtaining a sample from said surface;
   b) adding to said sample a hydrolytic enzyme for converting a carbohydrate that contains glucose to glucose, said hydrolytic enzyme comprising amylase; and
   c) detecting the presence or absence of glucose that has been derived in step b from said sample, wherein the presence of the glucose derived in step b from said sample is an indicator of said contamination on said surface.

51. The method of claim 50 wherein less than 10 minutes elapses between step b and step c.

52. The method of claim 50 wherein less than 5 minutes elapses between step b and step c.

53. The method of claim 50, further comprising adding to said sample a phosphorylase enzyme and a carbohydrate substrate to produce, in the presence of a phosphate in said sample, a reaction product of glucose and a phosphate-bound saccharide reaction product.

54. A method for monitoring the hygiene of a surface desired to be free of the presence of biological contamination, which method comprises the steps of:
   a) obtaining a sample from said surface;
   b) adding to said sample a hydrolytic enzyme for converting a carbohydrate that contains glucose to glucose, said hydrolytic enzyme comprising cellulase; and
   c) detecting the presence or absence of glucose that has been derived in step b from said sample, wherein the presence of the glucose derived in step b from said sample is an indicator of said contamination on said surface.

55. The method of claim 54 wherein less than 10 minutes elapses between step b and step c.

56. The method of claim 54 wherein less than 5 minutes elapses between step b and step c.

57. The method of claim 54, further comprising adding to said sample a phosphorylase enzyme and a carbohydrate substrate to produce, in the presence of a phosphate in said sample, a reaction product of glucose and a phosphate-bound saccharide reaction product.

58. A method for monitoring the hygiene of a surface desired to be free of the presence of biological contamination, which method comprises the steps of:
   a) obtaining a sample from said surface;
   b) introducing the sample onto a capillary-flow membrane containing reagents for production of glucose and components for colorimetric detection of glucose; and
   c) detecting the presence or absence of glucose that has been produced in step b from said sample, wherein the presence of the glucose produced in step b from said sample is an indicator of said contamination on said surface.

59. The method of claim 58 wherein said reagents comprise a hydrolytic enzyme.

60. The method of claim 58 wherein said reagents for production of glucose is a hydrolytic enzyme selected from the group consisting of amylase, invertase, beta-galactosidase, sucrase and cellulase.

61. The method of claim 58 wherein less than 10 minutes elapses between step b and step c.

62. The method of claim 58, further comprising adding to said sample a phosphorylase enzyme and a carbohydrate substrate to produce, in the presence of a phosphate in said sample, a reaction product of glucose and a phosphate-bound saccharide reaction product.

* * * * *